US00PP23635P3

(12) United States Plant Patent
Bak et al.

(10) Patent No.: US PP23,635 P3
(45) Date of Patent: May 28, 2013

(54) ***MEDINILLA* HYBRID PLANT NAMED 'BELLA'**

(50) Latin Name: ***Medinilla* sp.**
Varietal Denomination: BELLA

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 37 days.

(21) Appl. No.: 13/067,309

(22) Filed: May 24, 2011

(65) Prior Publication Data

US 2012/0304345 P1 Nov. 29, 2012

(51) Int. Cl.
*A01H 5/00* (2006.01)

(52) U.S. Cl.
USPC ..... Plt./263.1; Plt./226

(58) Field of Classification Search ..... Plt./226, Plt./263.1
See application file for complete search history.

(56) References Cited

PUBLICATIONS

Printout of application information from Community Plant Variety Office (CPVO) website for corresponding CPVO application No. 2010/2686 filed Nov. 29, 2010 (1 page). (http://www.cpvoextranet.cpvo.europa.eu).

Printout of Official Gazette (Staatscourant) of Mar. 12, 2010 from Netherlands Plant Breeders' Rights office website showing publication of corresponding Netherlands PBR application No. MDN5 filed Dec. 24, 2009, shown on p. 2 (11 pages). (https://zoek.officielebekendmakingen.nl).

*Primary Examiner* — Susan McCormick Ewoldt
(74) *Attorney, Agent, or Firm* — Foley & Lardner LLP

(57) ABSTRACT

A new and distinct *Medinilla* sp. plant named 'BELLA', characterized by an erect shrub plant, measuring about 50 cm in total height (when first flowering) and about 55 cm in diameter; green colored leaves, measuring about 20 cm in length and about 8 cm in width; pendulous panicles, measuring about 20 cm in length and about 15 cm in diameter, with pink (RHS 78D) flowers.

1 Drawing Sheet

Latin name of the genus and species of the plant claimed: *Medinilla* sp.

Variety denomination: 'BELLA'.

BACKGROUND OF THE INVENTION

The present invention relates to a new and distinct hybrid cultivar of *Medinilla* plant, botanically known as *Medinilla* sp., hereinafter referred to by the cultivar name 'BELLA'. The genus of *Medinilla* belongs to the Melastomataceae family.

The new *Medinilla* 'BELLA' is a product of a planned breeding program conducted by the inventors, Elly Bak and Nico D. M. Steur; in Assendelft, The Netherlands. The objective of the breeding program is to develop a new *Medinilla* variety with good growing habit and attractive inflorescence.

The new *Medinilla* 'BELLA' originated from a cross made in a controlled breeding program by the inventors in 2007 in Assendelft, The Netherlands. The female or seed parent is the *Medinilla* selection designated '82954514' (unpatented), and the male or pollen parent is the *Medinilla* selection designated '82957015' (unpatented). 'BELLA' was discovered and selected by the inventors in 2008, as a single flowering plant within the progeny of the stated cross in a controlled environment in Assendelft, The Netherlands.

Asexual reproduction of the new *Medinilla* hybrid 'BELLA' performed by vegetative means by cuttings was first performed in 2008, in Assendelft, The Netherlands. The first 'BELLA' plants propagated through the use of cuttings flowered in 2009, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'BELLA' which in combination distinguish this *Medinilla* hybrid as a new and distinct cultivar:

1. Solid growth habit;
2. Erect shrub plant, measuring about 50 cm in height (above the pot when first flowering);
3. Green colored leaves, measuring about 20 cm in length and about 8 cm in width;
4. Pendulous panicles with pink (RHS 78D) colored flowers;

Of the many commercial cultivars known to the present inventors, the most similar in comparison to the new *Medinilla* 'BELLA' is the *Medinilla magnifica* 'PINATUBO' (unpatented). Plants of the new *Medinilla* 'BELLA' differ from plants of *Medinilla* 'PINATUBO' primarily in leaf size, bract size, and inflorescence color. Plants of 'BELLA' have smaller leaves and bracts than plants of 'PINATUBO'. Additionally, plants of 'BELLA' have darker pink inflorescence (RHS 75B) than plants of 'PINATUBO' (RHS 72C).

BRIEF DESCRIPTION OF THE PHOTOGRAPHS

The accompanying photograph illustrates the overall appearance of the new *Medinilla* 'BELLA' showing the colors as true as is reasonably possible with colored reproductions of this type. Colors in the photograph may differ slightly from the color values cited in the detailed botanical description which accurately describes the color of 'BELLA'.

FIG. 1 shows a side view perspective of a typical potted flowering plant of 'BELLA' at about 50 weeks from potting.

DETAILED BOTANICAL DESCRIPTION

'BELLA' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Medinilla* 'BELLA' as grown in a greenhouse in Assendelft, The Netherlands, under conditions which closely approximate those generally used in commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'BELLA' described is about 50 weeks from potting.

Classification:

*Botanical.*—*Medinilla* sp.

Parentage:

*Female parent.*—*Medinilla* selection designated '82954514' (unpatented).

*Male parent.*—*Medinilla* selection designated '82957015' (unpatented).

Propagation: Cuttings.

Plant:

*General appearance and form.*—Height: About 50 cm. Diameter: About 55 cm. Shape: Erect shrub.

*Plant type.*—Epiphytic.

*Growth habit.*—Stem.

*Plant vigor.*—Good.

*Flowering season.*—From April until October.

*Cold tolerance.*—Frost tender, temperatures below 5° C. may damage plants.

*Fragrance.*—None.

*Stem.*—Shape: Winged. Diameter: About 10 mm. Width (of wings): About 3 mm. Length of internodes: About 10 to 12 cm. Color: Dark Green, RHS 143A with lignified parts RHS 199B.

Foliage:

*Quantity.*—About 30-35.

*Size.*—Length: About 15-20 cm. Width: About 8 cm.

*Leaf arrangement.*—Opposite.

*Leaf attachment.*—Petiolate.

*Overall shape.*—Elliptical.

*Apex shape.*—Cuspidate.

*Base shape.*—Acute.

*Margin.*—Entire.

*Texture.*—Smooth.

*Color.*—Leaf color can vary somewhat depending on growing conditions. Upper Surface: Glossy green, between RHS 137A and 139A. Lower Surface: Green, between RHS 137C and 143A.

*Venation.*—Appearance: Sunken. Pattern: Parallel. Color: Upper Surface: Yellow-Green, RHS 144C. Lower Surface: Red-Purple, RHS 60A.

Inflorescence:

*Shape.*—Pendulous panicles.

*Amount.*—About 2-6 (depending on the size of the plant).

*Size.*—Length: About 20 cm. Width: About 15 cm.

*Color.*—Pink, closest to RHS 78D.

*Corolla.*—Number: about 120 per panicle.

*Flower buds.*—Length: 10 mm. Width: 6 mm. Color: Red-Purple, RHS 64B.

*Petals.*—Number: 4 per flower. Length: 12 mm. Width: 8 mm. Overall Shape: obovate, asymmetrical. Apex Shape: obtuse. Color: Upper surface: pink, closest to RHS 78D. Lower surface: pink, closest to RHS 78D. Sepals: growth together, enclosing the ovary. Color: red purple, closest to RHS 57C.

*Peduncle.*—Length: Approx. 12 cm. Diameter: Approx. 3.5 mm. Color: Basal color Light Green, RHS 144B, changing to dark red-purple, RHS 59B.

*Pedicel.*—Length: Approx. 40 mm to approx. 5 mm (at the top). Diameter: Approx. 2 mm. Color: Red-Purple, RHS 57B.

*Bracts.*—Quantity: 4 per crown. Arrangement: verticillate. Size: Length: about 22 mm. Width: about 13 mm. Overall shape: elliptical. Color: Dark Green, RHS 143C with a red-purple flush, RHS 61A.

Reproductive organs:

*Androecium.*—Stamen: Number: 10 per flower. Length: 6 mm. Diameter: 1 mm. Color: light yellow, closest to RHS 11C. Anther: Length: 10 mm. Color: violet, closest to RHS 87B, with a yellow base. Pollen: Amount: not visible.

*Gynoecium.*—Pistil: Number: 1 per flower. Length: 20 mm. Stigma: Width: <1 mm. Color: white, too small to qualify RHS value. Style: Length: 17 mm. Color: white, closest to RHS 155C. Ovary: Shape: round. Position: inferior. Length: 8 mm. Diameter: 6 mm. Color: white, closest to RHS 155C.

Seeds: No seeds produced.

Fruit: No fruit produced.

Disease/pest resistance: No observations made.

Disease/pest susceptibility: No observations made.

What is claimed is:

1. A new and distinct *Medinilla* plant named 'BELLA', as illustrated and described herein.

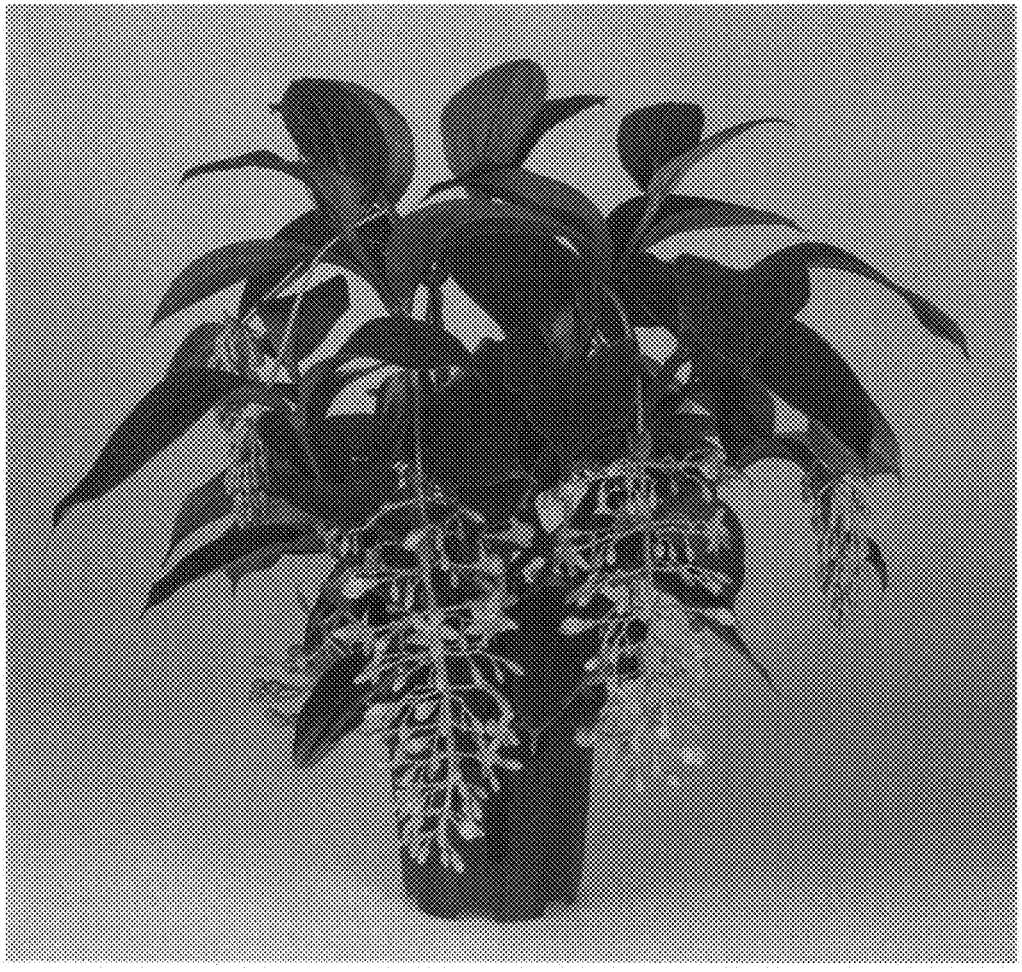

* * * * *